United States Patent [19]

Ariga et al.

[11] Patent Number: 5,663,256
[45] Date of Patent: Sep. 2, 1997

[54] THERMOSETTING AQUEOUS-TYPE EMULSION OF NADIMIDES

[75] Inventors: Hideya Ariga, Aichi-ken; Norio Futaesaku; Hiromitsu Baba, both of Ichihara, all of Japan

[73] Assignee: Maruzen Petrochemical Co., Ltd., Tokyo, Japan

[21] Appl. No.: 546,713

[22] Filed: Oct. 23, 1995

[30] Foreign Application Priority Data

Oct. 26, 1994 [JP] Japan ............................ 6-286026

[51] Int. Cl.⁶ .................. C08F 222/40; C07D 209/76
[52] U.S. Cl. .................. 526/262; 524/548; 528/322; 548/435
[58] Field of Search ............... 526/262; 548/435; 528/322; 524/548

[56] References Cited

U.S. PATENT DOCUMENTS

| | | | |
|---|---|---|---|
| 4,515,962 | 5/1985 | Renner | 526/262 |
| 4,579,916 | 4/1986 | Schmid et al. | 525/502 |
| 4,604,437 | 8/1986 | Renner | 526/259 |
| 4,666,997 | 5/1987 | Renner et al. | 526/262 |
| 4,678,849 | 7/1987 | Liu et al. | 526/259 |
| 4,709,047 | 11/1987 | Renner et al. | 526/259 |
| 4,728,742 | 3/1988 | Renner | 528/117 |
| 4,777,236 | 10/1988 | Kramer | 528/322 |
| 4,925,915 | 5/1990 | Mueller et al. | 528/353 |
| 5,023,339 | 6/1991 | Kato et al. | 548/401 |
| 5,496,893 | 3/1996 | Gagne et al. | 525/540 |
| 5,502,207 | 3/1996 | Futaesaku et al. | 548/435 |

OTHER PUBLICATIONS

Japanese Patent Laid–Open No. Sho 63 (1988) –170358 Derwent Publication.
Japanese Patent Laid–open No. Hei 7 (1995) 206991.

*Primary Examiner*—Paul R. Michl
*Assistant Examiner*—Olga Asinovsky
*Attorney, Agent, or Firm*—Melvin L. Stoltz

[57] ABSTRACT

A thermosetting aqueous-type emulsion of nadimide is disclosed. The emulsion comprises 1–70% by weight of an alkenyl-substituted nadimide, 0.1–20% by weight of protective colloid and/or surface-active agent and balance water. The emulsion is especially useful for making a paint, a coating material or an adhesive because the emulsion can easily be cured only by heating without forming any undesirable organic pollutants. In the past, various resins have been used together with organic solvents. However, because of the recent worldwide concern over the influence of organic solvents to pollution of the aerospace and underground environments, non-use or reduced-use of organic solvents is actively desired. Accordingly, developments of aqueous solution or aqueous-type emulsion of resins are desired. Until now there is no aqueous-type emulsion of a monomer of highly heat resistant polyimide.

21 Claims, No Drawings

THERMOSETTING AQUEOUS-TYPE EMULSION OF NADIMIDES

BACKGROUND OF THE INVENTION

1. Field of the Invention

The present invention relates to a thermosetting aqueous-type emulsion of nadimide prepared by dispersing an alkenyl-substituted nadimide in water. It can be used without an organic solvent or with a reduced amount of an organic solvent and is suitable for use as a paint, a coating material or an adhesive.

2. Description of the Prior Art

Conventionally, various resins have been used together with organic solvents in order to improve working performances by enhancing fluidity. However, because of the recent worldwide concern over the influence of organic solvents to pollution of the aerospace and underground environments, e.g. groundwater, non-use or reduced-use of organic solvents is actively promoted in the field of paints, coating materials and adhesives. The use of organic solvents is not desirable because it accompanies evaporation of large amounts of organic solvents in the air.

To make an aqueous-type emulsion of resin materials is a typical countermeasure for the non-use of organic solvents, and various aqueous-type resin emulsions are known in the art. With regard to imide resins which have excellent heat resistance, however, only known aqueous-type emulsions are those of maleimide compounds (for example, U.S. Pat. No. 5,023,339).

There are two types of maleimide compounds, one having two maleimide groups (e.g. bismaleimide) and the other having only one maleimide group (e.g. phenylmaleimide). The former is known to easily produce polyimide having excellent heat resistance only by heating. Whereas until now, it is not yet known that the latter can produce polyimide having excellent heat resistance only by heating.

The above-mentioned emulsion disclosed in U.S. Pat. No. 5,023,339 is the emulsion made from a compound having only one maleimide group, not a compound having two maleimide groups which is convertible into highly heat resistant polyimide. This emulsion, therefore, has no good applicability as a paint, a coating material, or an adhesive. That is, until now there is no aqueous-type emulsion of an imide compound which is convertible into a cured material only by removing water from the emulsion and by heating. If such an aqueous-type emulsion of imide can be prepared, it is usable as a paint, a coating material, or an adhesive. Development of such an aqueous-type emulsion has therefore been desired.

SUMMARY OF THE INVENTION

In view of this situation, an object of the present invention is to provide a thermosetting aqueous-type emulsion of imide prepared by dispersing a nadimide compound in water, which is useful as a paint, a coating material or an adhesive.

Other objects of the present invention will be apparent to those in the art from the detailed descriptions and examples given hereunder.

As a result of extensive studies in Order to achieve these objects, we have found that an aqueous-type emulsion of nadimide prepared by dispersing an alkenyl-substituted nadimide in water using a protective colloid or a surface-active agent, or both, can be cured with heat after removal of water, and is thus useful as a polyimide-type paint, coating material or adhesive exhibiting superior heat resistance. This finding has led to the completion of the present invention.

Thus, the gist of the present invention resides in a thermosetting aqueous-type emulsion of nadimide comprising 1–70% by weight of an alkenyl-substituted nadimide, 0.1–20% by weight of protective colloid and/or surface-active agent and balance water.

DETAILED DESCRIPTION OF THE INVENTION

Known alkenyl-substituted nadimide compounds disclosed in U.S. Pat. No. 4,515,962, U.S. Pat. No. 4,604,437, U.S. Pat. No. 4,728,742, U.S. Pat. No. 4,709,047 or Japanese Patent Laid-open No. Sho 63(1988)-170358 can be used in the present invention. Other various alkenyl-substituted nadimide compounds disclosed, for example, in Japanese Patent Laid-open No. Hei 7 (1995)-53516 which corresponds to U.S. Pat. No. 5,502,207 and Japanese Patent Laid-open No. Hei 7(1995)-206991 can also be used. These alkenyl-substituted nadimide compounds which can be used in the present invention are represented by the following formula (1).

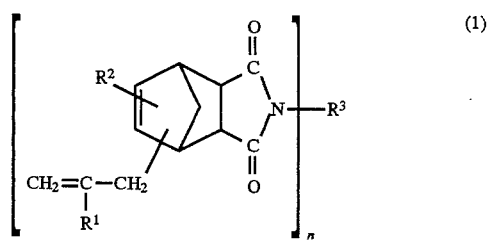

In the formula, $R^1$ and $R^2$ may be same or different and individually represent a hydrogen atom or a methyl group; n is an integer of 1 or 2; and when n is 1, $R^3$ represents a $C_1$–$C_{12}$ alkyl group, a $C_3$–$C_6$ alkenyl group, a $C_5$–$C_8$ cycloalkyl group, a $C_6$–$C_{12}$ monovalent aromatic group, a benzyl group, a group —{$(C_qH_{2q}O)_t$ $(C_rH_{2r}O)_u C_vH_{2v+1}$} (wherein q, r and v individually indicate an integer of 2–6, t is an integer of 0 or 1, and u denotes an integer of 1–30), or a group —$C_6H_4$—T—$C_6H_5$ (wherein T represents —$CH_2$—, —$C(CH_3)_2$—, —CO—, —O—, —S—, or —$SO_2$—), and when n is 2, $R^3$ represents a $C_2$–$C_{20}$ alkylene group, a $C_5$–$C_8$ cycloalkylene group, a group —{$(C_xH_{2x}O)_y$ $(C_zH_{2z}O)_w C_bH_{2b}$}— (wherein x, z, and b individually indicate an integer of 2–6, y is an integer of 0 or 1, and w denotes an integer of 1–30), a $C_6$–$C_{12}$ divalent aromatic group, a group —R—$C_6H_4$—(R')$_m$— (wherein m is an integer of 0 or 1 and R and R' may be the same or different and each individually represents a $C_1$–$C_4$ alkylene group or a $C_5$–$C_8$ cycloalkylene group), or a group —$C_6H_4$—A—$C_6H_4$— (wherein A represents —$CH_2$—, —$C(CH_3)_2$—, —CO—, —O—, —$OC_6H_4C(CH_3)_2C_6H_4O$—, —S—, or —$SO_2$—).

In the above formula (1), 1–3 hydrogen atoms in $R^3$ may be substituted by hydroxyl groups, carboxyl groups, amino groups, mercapto groups, carbamoyl groups or isocyano groups.

In the compounds represented by formula (1) above, nadimides having two alkenyl groups in the molecule are preferred. Compounds having n of 2, i.e., bisnadimides are more preferred. Further, among the bisnadimides, bisnadimides having $R^3$ of (i) a $C_2$–$C_{20}$ alkylene group, (ii) —R—$C_6H_4$—(R')$_m$— (wherein R, R' and m are as specified above) or (iii) —$C_6H_4$—A—$C_6H_4$— (wherein A is as specified above) are still more preferred. Among the bisnadimides mentioned above, N,N'-m-xylylene-bis(allylbicyclo[2.2.1] hept-5-ene-2,3-dicarboximide), bis[4-(allylbicyclo[2.2.1] hept-5-ene-2,3-dicarboximido)phenyl]methane and N,N'-hexamethylene-bis(allylbicyclo[2.2.1]hept-5-ene-2,3-dicarboximide) are especially preferred because they can be easily obtainable in the market. When n is 1, compounds having a $C_3$–$C_6$ alkenyl group as $R^3$ are preferred.

Given as examples of the asymmetric alkylene•phenylene group and asymmetric alkylene•phenylene•alkylene group which are within the scope of the chemical formula of —R—$C_6H_4$—(R')$_m$— appearing within the definition of $R^3$ when n is 2 in formula (1), are groups of the following formulas (2)–(6).

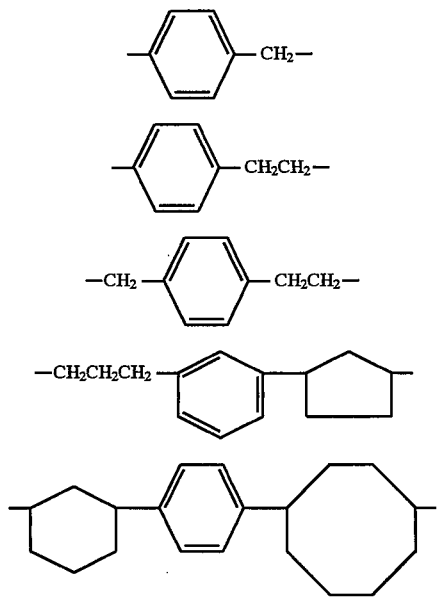

Typical examples of alkenyl-substituted nadimides represented by formula (1) are illustrated below:

When n is 1, following compounds can be shown:
N-methyl-allylbicyclo[2.2.1]hept-5-ene-2,3-dicarboximide, N-allyl-allylbicyclo[2.2.1]hept-5-ene-2,3-dicarboximide, N-cyclohexyl-allylbicyclo[2.2.1]hept-5-ene-2,3-dicarboximide, N-phenyl-allylbicyclo[2.2.1]hept-5-ene-2,3-dicarboximide and N-benzyl-allylbicyclo[2.2.1]hept-5-ene-2,3-dicarboximide.

When n is 2, following compounds can be shown:
N,N'-ethylene-bis(allylbicyclo[2.2.1]hept-5-ene-2,3-dicarboximide), N,N'-hexamethylene-bis(allylbicyclo[2.2.1]hept-5-ene-2,3-dicarboximide), N,N'-dodecamethylene-bis(allylbicyclo[2.2.1]hept-5-ene-2,3-dicarboximide), N,N'-cyclohexylene-bis(allylbicyclo[2.2.1] hept-5-ene-2,3-dicarboximide), 1,2-bis[3'-(allylbicyclo [2.2.1]hept-5-ene-2,3-dicarboximido)propoxy]ethane, bis [2'-[3"-(allylbicyclo[2.2.1]hept-5-ene-2,3-dicarboximido) propoxy]ethyl]ether, 1,4-bis[3'-(allylbicyclo[2.2.1]hept-5-ene-2,3-dicarboximido) propoxy]butane, N,N'-p-phenylene-bis(allylbicyclo[2.2.1]hept-5-ene-2,3-dicarboximide), N,N'-m-phenylene-bis(allylbicyclo[2.2.1]hept-5-ene-2,3-dicarboximide), N,N'-p-xylylene-bis(allylbicyclo[2.2.1] hept-5-ene-2,3-dicarboximide), N,N'-m-xylylene-bis (allylbicyclo[2.2.1]hept-5-ene-2,3-dicarboximide), N-[4-[2'-(allylbicyclo[2.2.1]hept-5-ene-2,3-dicarboximido)ethyl] phenyl]allylbicyclo[2.2.1]hept-5-ene-2,3-dicarboximide, 2,2-bis[4'-[4"-(allylbicyclo[2.2.1]hept-5-ene-2,3-dicarboximido)phenoxy]phenyl]propane, bis[4-(allylbicyclo[2.2.1]hept-5-ene-2,3-dicarboximido)phenyl] methane, bis[4-allylbicyclo[2.2.1]hept-5-ene-2,3-dicarboximido)phenyl]ether and bis[4-(allylbicyclo[2.2.1] hept-5-ene-2,3-dicarboximido)phenyl]sulfone.

The alkenyl-substituted nadimide compounds usable in the present invention are not limited to those enumerated above. These alkenyl-substituted nadimide compounds may be used either individually or in combination of two or more. Further, it is possible to use oligomers of an alkenyl-substituted nadimide compound.

When an emulsion suitable for producing coatings and adhesives having especially excellent heat resistance, hot water resistance and high temperature steam resistance is desired, it is preferable to use bisnadimides having an alkylene•phenylene group or an alkylene•phenylene•alkylene group as $R^3$.

Given as examples of the protective colloid usable in the present invention are polyvinyl alcohol, maleinized polyvinyl alcohol, water-soluble cellulose derivatives, such as ethylcellulose, methylcellulose, and hydroxyethylcellulose, starch derivatives, agar, gelatin, albumin, gum arabic, protalbinic acid, lisalbinic acid, alginic acid, styrene-maleic anhydride copolymers, maleinized liquid polybutadiene derivatives, naphthalene sulfonate/formaldehyde condensate, polyacrylic acid, salt of polyacrylic acid, polyacrylic amide, polyacrylate, and the like.

As the surface-active agent, anionic, cationic, nonionic, and amphoteric surface-active agents can be used.

Given as examples of anionic surface-active agents are alkylbenzenesulfonates such as sodium dodecylbenzenesulfonate, alkylnaphthalenesulfonates such as sodium dodecylnaphthalenesulfonate, salts of fatty acids such as sodium salts of fatty acid, salt of rhodinic acids, salts of dialkylsulfosuccinic acid, hydroxyalkanesulfonates, alkanesulfonates, alkyl sulfates, alkyl phosphates, polyoxyethylene alkylphenyl ether sulfates, and the like.

Cationic surface-active agents include, for example, alkylamine hydrochlorides, salts of dialkylamines, tetraalkylammonium salts such as tetraalkylammonium chlorides, alkylpyridinium salts, N,N'-dialkylmorpholinium salts, and the like.

Examples of nonionic surface-active agents include polyoxyethylene alkyl ether, polyoxyethylene alkylphenyl ether, polyoxyethylene polyoxypropylene glycol, partial esters of polyhydric alcohol with fatty acid, partial esters of polyoxyethylene modified polyhydric alcohol with fatty acid, diethanolamides of fatty acid, and the like.

Examples of amphoteric surface-active agents include carboxybetaines, imidazolines, esters of amidosulfuric acid, and the like.

The protective colloids and surface-active agents which can be used in the present invention are not limited to these compounds. The protective colloids and surface-active agents are used individually or in combination of two or more of them from each group. In addition, a combination of a protective colloid and a surface-active agent is also acceptable.

The thermosetting aqueous-type emulsion of the present invention is made up of 1–70% by weight, preferably 20–60% by weight, of alkenyl-substituted nadimides, 0.1–20% by weight, preferably 2–15% by weight, of protective colloids and/or surface-active agents, and balance water.

The thermosetting aqueous-type emulsion of the present invention can be prepared, for example, by the following process. Specified amounts of water, an alkenyl-substituted nadimide, a protective colloid and/or a surface-active agent are charged into a stirring vessel, such as a homomixer, and preliminarily mixed for a short period of time at a temperature within a range of from room temperature to 90° C. The mixture is successively treated in a colloid mill, sand mill, ball mill, or homogenizer. Although the thermosetting aqueous-type emulsion is sufficiently homogeneous without using an organic solvent, it is possible, if the environment of use permits, to dissolve the alkenyl-substituted nadimide in a small amount of an organic solvent in advance before the emulsion is prepared. Toluene, xylene, N-methyl-2-pyrrolidone, and the like are given as examples of the organic solvents.

The alkenyl-substituted nadimide can be finely dispersed in the thermosetting aqueous-type emulsion of the present invention with ease. The average particle size of the alkenyl-substituted nadimide in the emulsion can be arbitrarily controlled by adjusting the amount of water, the types and amounts of the protective colloid and/or surface-active agent. In addition, either a w/o-type emulsion or an o/w-type emulsion can be made by adjusting the amount of water.

The thermosetting aqueous-type emulsion of the present invention thus prepared can be used for a variety of applications by removing water and the organic solvent, if the latter is used, and then curing the residue with heat. Because the emulsion has a low viscosity even at a high concentration of the alkenyl-substituted nadimide of, e.g. 50–70% by weight, it can be easily applied to the object to be painted using a brush or a spatula, and is thus useful as an adhesive, a coating material, a paint, and the like.

Although the thermosetting aqueous-type emulsion of the present invention is well cured without using a catalyst, it is possible to use a curing catalyst to accelerate the curing reaction. Among organic peroxides, inorganic peroxides, onium salts, cationic catalysts, and organic group-containing metal compounds, those which are not decomposed with water can be used as the curing catalyst.

As the organic peroxides, for example, t-butyl hydroperoxide, cyclohexyl hydroperoxide, and cumene hydroperoxide can be cited.

As the inorganic peroxides, for example, ammonium peroxodisulfate and potassium peroxodisulfate can be cited.

As the onium salts, for example, ammonium compounds, such as benzyltriethylammonium chloride, tetra-n-butylammonium perchlorate and tetraethylammonium tetrafluoroborate; phosphonium compounds, such as methyltriphenylphosphonium iodide, benzyltriphenylphosphonium chloride, tetraphenylphosphonium bromide and 3-bromopropyltriphenylphosphonium bromide; arsonium compounds, such as benzyltriphenylarsonium chloride; oxonium compounds, such as triphenyloxonium chloride and triphenyloxonium bromide; sulfonium compounds, such as dimethylphenacylsulfonium hexafluorophosphate and dimethylphenacylsulfonium tetrafluoroborate; and iodonium compounds, such as diphenyliodonium perchlorate, diphenyliodonium tetrafluoroborate, diphenyliodonium hexafluoroarsenate, diphenyliodonium hexafluorophosphate and diphenyliodonium hexafluoroantimonate can be cited.

As the cationic catalysts of the above, for example, acids or Brønsted acids which can give protons, and esters thereof or amine complexes thereof, such as sulfuric acid•pyridine complex, dimethyl phosphate, diphenyl phosphate, p-toluenesulfonic acid, p-toluenesulfonic acid•pyridine complex, m-nitrobenzenesulfonic acid-pyridine complex, α- or β-naphthalenesulfonic acid, and N-(2-benzenesulfonylhydroxyethyl)-allyl-bicyclo[2.2.1]hept-5-ene-2,3-dicarboximide (ANI-BsE) can be cited.

As the organic group-containing metal compounds, for example, acetyl acetonates, carboxylic acid salts, alcoholates, chelate compounds and organometallic compounds of metals such as Ti, V, Cr, Mn, Fe, Co, Ni, Cu, Zr, Mo, Ru, Rh, La, Ce, Hf, Ta and W, and preferably acetyl acetonates of V, Mn, Fe and Ce can be cited. Incidentally, joint use of the organic peroxides and the organic group-containing metal compounds is also applicable.

The amount of the curing catalyst used in the reaction can be determined from a wide range with no specific limitations, usually, from a range of 0.005–10% by weight, and preferably 0.01–5% by weight, of the amount of the alkenyl-substituted nadimide.

Although curing of the thermosetting aqueous-type emulsion of the present invention can be accelerated by the use of the curing catalyst mentioned above, use of curing catalyst is not so preferable, if the production of very strong coatings and adhesions are desired. The use of curing catalyst has a tendency to decrease the strength of coatings and adhesions.

Various additives may be added to the thermosetting aqueous-type emulsion of the present invention depending on the applications to which it is used. Fillers, modifiers, pigments, dyestuffs and the like can be given as examples of the additives.

Carbon black or commonly used pigments such as titanium oxide may be added to the coating material of the present invention.

The adhesive or the coating material of the present invention can be used for adhering or coating metals, such as steel, aluminum, or copper; glass, resin, cement, ceramics, and the like.

Further, although the thermosetting aqueous-type emulsion of the present invention can be used independently, it is possible depending on the applications to use it together with a polymer or a monomer which is copolymerizable therewith. Examples of the polymers or the monomers which are copolymerizable with alkenyl-substituted nadimide are vinyl compounds, cyclic olefins, phenol resins, and the like.

As vinyl compounds, such as o-divinylbenzene, m-divinylbenzene, p-divinylbenzene, divinylnaphthalene, divinyl adipate, 1,5-hexadiene-3,4-diol, 1,3-butadiene, 1,4-pentadiene, 1,3-divinyl-1,1,3,3-tetramethyldisiloxane, 3,9-divinyl-2,4,8,10-tetraoxaspiro[5.5]undecane, di-2-propenyl 1,2-benzenedicarboxylate, di-2-propenyl 1,3-benzenedicarboxylate, N-2-propenyl-2-propene-1-amine, 1,1'-oxybisethene, 3,3'-oxybis-1-propene, 1,1'-thiobisethene, 1,1'-sulfonylbisethene, 2,2-dichloro-N,N-di (2-propenyl) acetamide, di-1-propenyldisulfide, ethylvinylbenzene, styrene, α-methylstyrene, vinylnaphthalene, acrylonitrile, vinyl esters of fatty acid, acrylic acid, methacrylic acid, maleic acid, fumaric acid, itaconic acid and esters of these acids can be cited.

Given as examples of cyclic olefins are cyclopentene, cyclohexene, 4-vinylcyclohexene, cycloheptene, cyclooctene, cyclododecene, cyclopentadiene, dicyclopentadiene, 1,3-cyclohexadiene, 1,3-cycloheptadiene, 1,5-cyclooctadiene and indene.

Among these, divinyl compounds are more preferred than monovinyl compounds or cyclic olefins in view of reactivity of the resulting emulsion and workability in the preparation of the emulsion. Among divinyl compounds, o-divinylbenzene, p-divinylbenzene, m-divinylbenzene, di-2-propenyl 1,2-benzenedicarboxylate, di-2-propenyl 1,3-benzenedicarboxylate and 3,9-divinyl-2,4,8,10- tetraoxaspiro[5.5]undecane are preferred. These compounds can be used either singly or as a mixture of two or more.

Included in phenol resins are, beside typical phenol resins prepared from a phenolic compound and formaldehyde or a formaldehyde-forming compound, aromatic hydrocarbon resins such as xylene-formaldehyde resin, a reaction product of xylene resin and phenol, phenol-alkyl resin synthesized by the reaction of phenol and dimethoxy xylene, phenol-dicyclopentadiene resin obtained by the reaction of phenol and dicyclopentadiene, resins obtained by the polymerization of paravinyl phenol or isopropenyl phenol, bisphenol A, bisphenol F and the like.

Of course, any combination of vinyl compounds, cyclic olefins and phenol resins can be used.

The thermosetting aqueous-type imide emulsion obtained in the present invention can be cured easily to form a strong heat resistant solid material by heating after removal of water from the emulsion. It is therefore useful as a paint, a coating material, an adhesive, and the like requiring strong heat resistance. In addition, handling of the emulsion is easy because it has excellent storage stability.

DESCRIPTION OF THE PREFERRED EMBODIMENTS

The present invention will be illustrated in more detail by examples which are not intended to be limiting thereof.

EXAMPLE 1

Into a 1 liter homomixer, 250 cc of water was placed and then 14 g of potassium rhodinate, $_{11}$ g of polyoxyethylene nonylphenyl ether, and 225 g of N,N'-m-xylylene-bis(allylbicyclo[2.2.1]hept-5-ene-2,3-dicarboximide) (softening point: 45° C., hereinafter referred to as BANI-X) were successively added, heated at 70° C., and stirred to homogenize. The mixture was then transferred to a pressure homogenizer and emulsified to obtain an emulsion with an average particle size of 1.0 μm.

No precipitate was produced in this emulsion after storing for 3 months.

EXAMPLE 2

Into a 1 liter homomixer, 250 cc of water was placed, and then 15 g of polyvinyl alcohol and 5 g of sodium dodecyl-benzene sulfonate were successively added to it, following which 200 g of bis[4-(allylbicyclo[2.$_{2.1}$]hept-5-ene-2,3-dicarboximido) phenyl]methane (softening point: 150° C.) was added while stirring. The mixture was transferred to a ball mill and emulsified to obtain an emulsion with an average particle size of 0.8 μm.

No precipitate was produced in this emulsion after storing for 3 months.

EXAMPLE 3

Into a 1 liter homomixer, 225 cc of water was placed, and then 200 g of N,N'-hexamethylene-bis(allylbicyclo[2.2.1]hept-5-ene-2,3-dicarboximide) (softening point: 20° C.), 45 g of polyoxyethylene nonylphenyl ether, and 30 g of polyoxyethylene polyoxypropylene glycol were added while stirring. The mixture was heated at 50° C., and stirred to homogenize. The mixturte was then transferred to a pressure homogenizer and emulsified to obtain an emulsion with an average particle size of 0.3 μm.

No precipitate was produced in this emulsion after storing for 3 months.

EXAMPLE 4

The same experiment as in Example 2 was carried out, except that 15 g of maleinized liquid polybutadiene derivative was used instead of 15 of polyvinyl alcohol, to obtain an emulsion with an average particle size of 0.8 μm.

No precipitate was produced in this emulsion after storing for 3 months.

EXAMPLE 5

The same experiment as in Example 3 was carried out, except that the amounts of polyoxyethylene nonylphenyl ether and polyoxyethylene polyoxypropyrene glycol used were 19 g and 13 g, respectively. An emulsion with an average particle size of 0.5 μm was obtained.

No precipitate was produced in this emulsion after storing for 3 months.

EXAMPLE 6

Multiple sheets of soft steel plates (length: 10 cm, width: 2.5 cm, thickness: 0.2 cm) were polished at one of the ends with No. 240 abrasive paper. Trash and oily components were washed out with acetone and the BANI-X emulsion prepared in Example 1 was applied to the plates for a length of 1.3 cm from the end using an applicator. After removing water by heating at 120° C. for 1 hour, the two soft steel plates were layered respectively with the coated portions faced vis-a-vis. The BANI-X was cured at 250° C. for 2 hours while fastening the plates with a clip. Tensile-shearing tests (JIS-K6850) were carried out at room temperature and 250° C. using the test pieces thus prepared. The results of the tensile shear adhesive strength obtained at room temperature was 242 Kg/cm$^2$ and at 250° C. was 157 Kg/cm$^2$. Incidentally, the results obtained by using a solution of BANI-X in methyl ethyl ketone at room temperature was 202 Kg/cm$^2$ and at 250° C. was 157 Kg/cm$^2$.

EXAMPLE 7

The emulsion of BANI-X prepared in Example 1 was coated to a soft steel plate (length: 15 cm, width: 7 cm, thickness: 0.08 cm) using an applicator, and heated at 120° C. for 1 hour to remove water. A coating with a thickness of 15 μm was obtained by further heating at 200° C. for 30 minutes.

After allowing to stand at room temperature for 24 hours, a cross-cut adhesion test (JIS-K5400) was carried out. A result of 100/100 was obtained, indicating that no peel-off occurred.

EXAMPLE 8

Five grams (5 g) of an aqueous emulsion containing 40% by weight of titanium oxide (average particle size: 0.3 μm) was added to 10 g of the emulsion of BANI-X prepared in Example 1, and the mixture was sufficiently mixed wth stirring. A coating with a thickness of 15 μm was prepared from this mixture in the same manner as in Example 7.

After allowing to stand at room temperature for 24 hours, a cross-cut adhesion test (JIS-K5400) was carried out. A result of 100/100 was obtained, indicating that no peel-off occurred.

We claim:

1. A thermosetting aqueous-type emulsion of nadimide consisting essentially of between about 20 and 60% by weight of an alkenyl-substituted nadimide, between about 0.1 and 20% by weight of at least one ingredient selected from the group consisting of protective colloids and surface-active agents and water forming the balance.

2. The thermosetting aqueous-type emulsion of claim 1, wherein the amount of said ingredient is between about 2 and 15% by weight.

3. The thermosetting aqueous-type emulsion of claim 1, wherein said emulsion further contains curing catalyst selected from the group consisting of organic peroxides, inorganic peroxides, onium salts, cationic catalysts and organic group-containing metal compounds.

4. The thermosetting aqueous-type emulsion of claim 3, wherein the amount of said curing catalyst is within a range of 0.005–10% by weight based on the amount of said nadimide.

5. The thermosetting aqueous-type emulsion of claim 1, wherein said emulsion further contains a copolymerizable component selected from the group consisting of vinyl group containing compounds, cyclic olefins, and phenol compounds.

6. The thermosetting aqueous-type emulsion of claim 1, wherein said alkenyl-substituted nadimide has following chemical structure:

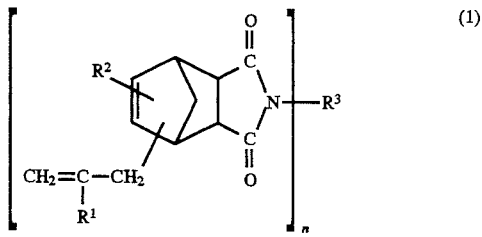

in the formula, $R^1$ and $R^2$ may be same or different and individually represent a hydrogen atom or a methyl group; n is an integer of 1 or 2; and when n is 1, $R^3$ represents a $C_1$–$C_{12}$ alkyl group, a $C_3$–$C_6$ alkenyl group, a $C_5$–$C_8$ cycloalkyl group, a $C_6$–$C_{12}$ monovalent aromatic group, a benzyl group, a group —{$(C_qH_{2q}O)_t$ $(C_rH_{2r}O)_u C_vH_{2v+1}$} (wherein q, r and v individually indicate an integer of 2–6, t is an integer of 0 or 1, and u denotes an integer of 1–30), or a group —$C_6H_4$—T—$C_6H_5$ (wherein T represents —$CH_2$—, —$C(CH_3)_2$—, —CO—, —O—, —S—, or —$SO_2$—), and when n is 2, $R^3$ represents a $C_2$–$C_{20}$ alkylene group, a $C_5$–$C_8$ cycloalkylene group, a group —{$(C_xH_{2x}O)_y$ $(C_zH_{2z}O)_w C_bH_{2b}$}— (wherein x, z, and b individually indicate an integer of 2–6, y is an integer of 0 or 1, and w denotes an integer of 1–30), a $C_6$–$C_{12}$ divalent aromatic group, a group —R—$C_6H_4$—(R')$_m$— (wherein m is an integer of 0 or 1 and R and R' may be the same or different and each individually represents a $C_1$–$C_4$ alkylene group or a $C_5$–$C_8$ cycloalkylene group), or a group —$C_6H_4$—A—$C_6H_4$— (wherein A represents —$CH_2$—, —$C(CH_3)_2$, —CO—, —O—, —$OC_6H_4C(CH_3)_2C_6H_4O$—, —S—, or —$SO_2$—); and 1–3 hydrogen atoms in $R^3$ can be substituted by hydroxyl groups, carboxyl groups, amino groups, mercapto groups, carbamoyl groups or isocyano groups.

7. The thermosetting aqueous-type emulsion of claim 6, wherein said alkenyl-substituted nadimide has two alkenyl groups in the molecule.

8. The thermosetting aqueous-type emulsion of claim 7, wherein n is 1, and $R^3$ is a $C_3$–$C_6$ alkenyl group.

9. The thermosetting aqueous-type emulsion of claim 7, wherein n is 2.

10. The thermosetting aqueous-type emulsion of claim 9, wherein $R^3$ is selected from the group consisting of (i) $C_2$–$C_{20}$ alkylene group, (ii) —R—$C_6H_4$—(R')$_m$— (wherein m is an integer of 0 or 1 and R and R' may be the same or different and each individually represents a $C_1$–$C_4$ alkylene group or a $C_5$–$C_8$ cycloalkylene group) and (iii) —$C_6H_4$—A—$C_6H_4$— (wherein A represents —$CH_2$—, —$C(CH_3)_2$—, —CO—, —O—, —$OC_6H_4C(CH_3)_2C_6H_4O$—, —S—, or —$SO_2$—).

11. The thermosetting aqueous-type emulsion of claim 10, wherein said alkenyl-substituted nadimide is selected from the group consisting of N,N'-m-xylylene-bis(allylbicyclo[2.2.1]hept-5-ene-2,3-dicarboximide), bis(4-(allylbicyclo[2.2.1]hept-5-ene-2,3-dicarboximido)phenyl)methane and N,N'-hexamethylene-bis(allylbicyclo[2.2.1]hept-5-ene-2,3-dicarboximide).

12. The thermosetting aqueous-type emulsion of claim 1, wherein said protective colloid is polyvinyl alcohol or maleinized liquid polybutadiene.

13. The thermosetting aqueous-type emulsion of claim 1, wherein said surface-active agent is selected from the group consisting of an anionic surface-active agent, a cationic surface-active agent, a nonionic surface-active agent, and an amphoteric surface-active agent.

14. The thermosetting aqueous-type emulsion of claim 13, wherein said surfce-active agent is salt of rhodinic acid, salt of alkylbenzene sulfonic acid, polyoxyethylene alkylphenyl ether or polyoxyethylene polyoxypropylene glycol.

15. The thermosetting aqueous-type emulsion of claim 11, wherein said protective colloid or said surface-active agent is selected from the group consisting of polyvinyl alcohol, maleinized liquid polybutadiene, salt of rhodinic acid, salt of alkylbenzene sulfonic acid, polyoxyethylene alkylphenyl ether and polyoxyethylene polyoxypropylene glycol.

16. A thermosetting aqueous-type emulsion of nadimide comprising between about 20 and 60% by weight of an alkenyl-substituted nadimide, between about 0.1 and 20% by weight of at least one ingredient selected from the group consisting of protective colloids and surface-active agents and between about 20 and 79.9% by weight of water.

17. The thermosetting aqueous-type emulsion of claim 16, wherein the amount of said ingredient is between about 2 and 15% by weight.

18. The thermosetting aqueous-type emulsion of claim 16, wherein said emulsion further contains curing catalyst selected from the group consisting of organic peroxides, inorganic peroxides, onium salts, cationic catalysts and organic group-containing metal compounds.

19. The thermosetting aqueous-type emulsion of claim 18, wherein the amount of said curing catalyst is within a range of 0.005–10% by weight based on the amount of said nadimide.

20. The thermosetting aqueous-type emulsion of claim 16, wherein said emulsion further contains a copolymerizable component selected from the group consisting of vinyl group containing compounds, cyclic olefins, and phenol compounds.

21. The thermosetting aqueous-type emulsion of claim 16, wherein said alkenyl-substituted nadimide has the following chemical structure:

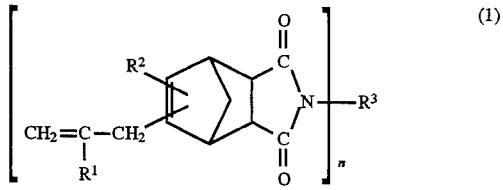

In the formula, $R^1$ and $R^2$ may be the same or different and individually represent a hydrogen atom or a methyl group; n is an integer of 1 or 2; and when n is 1, $R^3$ represents a $C_1$–$C_{12}$ alkyl group, a $C_3$–$C_6$ alkenyl group, a $C_5$–$C_8$ cycloalkyl group, a $C_6$–$C_{12}$ monovalent aromatic group, a benzyl group, a group —{$(C_qH_{2q}O)_t(C_rH_{2r}O)_uC_vH_{2v+1}$} (wherein q, r and v individually indicate an integer of 2–6, t is an integer of 0 or 1, and u denotes an integer of 1–30), or a group —$C_6H_4$—T—$C_6H_5$ (wherein T represents —$CH_2$—, —$C(CH_3)_2$—, —CO—, —O—, —S—, or —$SO_2$—), and when n is 2, $R^3$ represents a $C_{2-C20}$ alkylene group, a $C_5$–$C_8$ cycloalkylene group, a group —{$(C_xH_{2x}O)_y(C_zH_{2z}O)_wC_bH_{2b}$}— (wherein x, z, and b individually indicate an integer of 2–6, y is an integer of 0 or 1, and w denotes an integer of 1–30), a $C_6$–$C_{12}$ divalent aromatic group, a group —R—$C_6H_4$—(R')$_m$— (wherein m is an integer of 0 or 1 and R and R' may be the same or different and each individually represents a $C_1$–$C_4$ alkylene group or a $C_5$–$C_8$ cycloalkylene group), or a group —$C_6H_4$—A—$C_6H_4$— (wherein A represents —$CH_2$—, —$C(CH_3)_2$—, —CO—, —O—, —$OC_6H_4C(CH_3)_2C_6H_4O$—, —S—, or —$SO_2$—); and 1–3 hydrogen atoms in $R^3$ can be substituted by hydroxyl groups, carboxyl groups, amino groups, mercapto groups, carbamoyl groups or isocyano groups.

* * * * *